(12) United States Patent
Cook et al.

(10) Patent No.: US 6,761,855 B1
(45) Date of Patent: Jul. 13, 2004

(54) COLUMN FOR SOLID PHASE PROCESSING

(75) Inventors: Ronald M. Cook, Novato, CA (US); Rand Dill, Corte Madera, CA (US)

(73) Assignee: Biosearch Technologies, Inc., Nevato, CA (US)

(*) Notice: Subject to any disclaimer, the term of this patent is extended or adjusted under 35 U.S.C. 154(b) by 95 days.

(21) Appl. No.: 10/011,966

(22) Filed: Nov. 5, 2001

(51) Int. Cl.⁷ .............................................. G01N 30/60
(52) U.S. Cl. ........................... 422/70; 422/11; 422/102; 73/61.53; 210/198.2
(58) Field of Search ..................... 422/70, 101, 102; 210/198.2, 656; 73/61.53

(56) References Cited

U.S. PATENT DOCUMENTS

| | | | |
|---|---|---|---|
| 3,630,683 A | * 12/1971 | Robb ........................... | 422/70 |
| 4,046,145 A | * 9/1977 | Choksi et al. ............... | 604/407 |
| 4,214,993 A | * 7/1980 | Forsythe, Jr. et al. ....... | 210/282 |
| 4,238,196 A | * 12/1980 | Acuff et al. ................... | 436/67 |
| 4,249,530 A | * 2/1981 | Millet .......................... | 604/192 |
| 4,270,921 A | * 6/1981 | Graas .......................... | 436/67 |
| 4,341,635 A | * 7/1982 | Golias .......................... | 210/656 |
| 4,787,971 A | * 11/1988 | Donald ........................ | 210/198.2 |
| 4,892,710 A | * 1/1990 | Wong et al. ................. | 422/102 |
| 5,037,544 A | * 8/1991 | Snyder ........................ | 210/198.2 |
| 5,273,656 A | 12/1993 | Anderson et al. | |
| 5,413,708 A | * 5/1995 | Huse et al. ............... | 210/198.2 |
| 5,419,874 A | 5/1995 | Coassin et al. | |
| 5,439,593 A | * 8/1995 | Price ........................... | 210/660 |
| 5,869,643 A | 2/1999 | Chatelain et al. | |
| 6,103,195 A | * 8/2000 | Shukla et al. ................. | 422/70 |
| 6,177,008 B1 | * 1/2001 | Treiber et al. ........... | 210/198.2 |
| 6,177,009 B1 | * 1/2001 | Sieber et al. ............ | 210/198.2 |

* cited by examiner

*Primary Examiner*—Jan M. Ludlow
(74) *Attorney, Agent, or Firm*—Townsend Townsend and Crew LLP

(57) ABSTRACT

The present invention is directed to an improved column for use in solid phase synthesis or purification. In a specific embodiment, the column is a disposable plastic column for use in solid phase synthesis or purification of complex chemicals, such as biomolecules and more specifically oligonucleotides. In some embodiments, the column has a top orifice with a sufficient diameter so that a fluid line or a multiple fluid line bundle may dispense fluids into the column with great efficiency. The column has an upper cavity portion configured and sized to render it compatible with dispensing pippetors, so that it can be used as a pipette tip or a pipettor can be used to aspirate the column. The column has a lower cavity portion with a shoulder for ready placement of a lower frit to contain the solid support in a central cavity portion of the column. An upper frit can be conveniently placed in the central cavity portion to seal the solid phase resin. The lower end tip of the column is configured as a luer-type fitting to provide a male luer connection. The upper cavity portion is configured to interface with the male luer of another column, so that two or more columns to be connected in series.

19 Claims, 3 Drawing Sheets

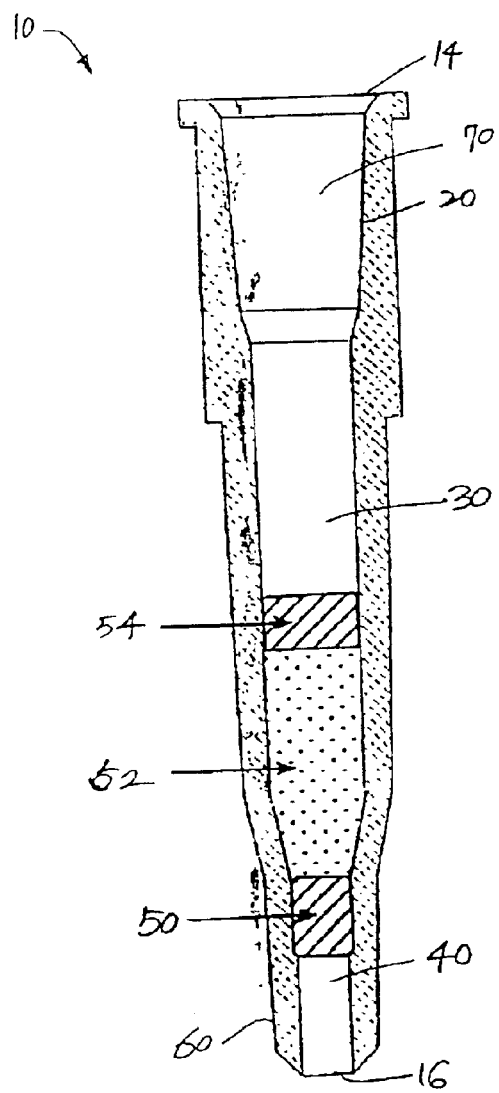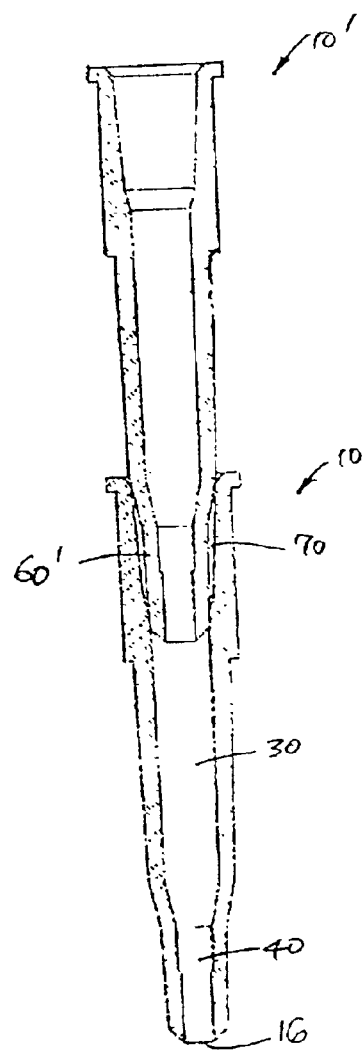
FIG. 2
FIG. 3

COLUMN FOR SOLID PHASE PROCESSING

BACKGROUND OF THE INVENTION

The present invention relates generally to solid phase processing and, more particularly to a column for use in solid phase processing including solid phase synthesis and purification of complex chemicals such as oligonucleotides and the like.

A variety of separative, synthetic, and enzymatic or otherwise catalytic processes use beds of particulate material with transport of reactants, reagents and products or eluants in solution through the bed. In addition, many reactions are known in which the products are separated by concentration in one of two or more phases. These processes include, among others, ion exchange chromatography, gel filtration, ion exclusion chromatography, affinity chromatography, separations based on hydrophobicity, purification based on hybridization, peptide synthesis, oligonucleotide synthesis, and polysaccharide synthesis including combinations of the last three. These processes may be carried out on a small scale for analytical purposes or process design, and are then often scaled up for preparative work. In nearly all examples the solid phase particulates are packed in a closed column with a porous frit on the lower end, an optional frit at the top, and with fluid-connections at both ends so that liquid can flow in either direction through the bed. To achieve efficiency and high resolution with solid phase supports, all volume elements of all fluids should flow through paths of identical composition and nearly identical length, and all particles in the bed should be exposed to the same succession of liquids under the same conditions.

In solid phase systems, some interaction occurs between the solutes run through the bed and the particles composing the bed. This interaction may be based on secondary forces (ionic, hydrophobic, or on immunochemical interactions, or base pairing) or primary valencies as when amino acids or nucleotides are added to a growing chain on the solid phase support, or when immobilized enzymes cleave substrates flowing through the bed, or when enzymes in solution react with substrates attached to the packing. In addition, solvents or reagents of successively differing composition which dissociate adsorbed or otherwise attached bound molecular species, or which cleave off protective groups, or compounds including polymers which have been synthesized on the support may be made to flow through the support. The dissociated or cleaved substances then are free to flow out of the bed in flowing liquid.

In particular, nucleic acid synthesis (generally referred to as "DNA synthesis") is the process of constructing synthetic single-stranded oligonucleotide through linking of nucleotide, the basic building blocks for DNA. In an automated system, the various steps are carried out by a reagent delivery system which dispenses a number of chemical reagents in a predetermined sequence in a cycle into a synthesis reaction column containing the solid-phase support, according to instructions from the system controller or computer. After the desired number of cycles have been completed, the synthesized oligonucleotide is separated from the reaction column and collected in a vial. This step is generally referred to as "cleavage". The oligonucleotide may further be subject to a step generally referred to as "deprotection" to complete isolation of the oligonucleotide. In a process for synthesizing polynucleotides on a solid support, the solid support traditionally consists of glass beads of controlled porosity (CPG) or, more generally, of particles of a functionalized inorganic or organic polymer.

The isolation of oligonucleotide involves the treatment of the solid bound oligonucleotide with a cleavage and/or deprotection reagent. Typically, this reagent is concentrated ammonia solution in water but can be other homogeneous or heterogeneous solutions of appropriate bases, alcohols and water. The cleavage and deprotection process is typically performed in two steps. The cleavage of the oligonucleotide is performed at room temperature for approximately one hour before decanting the mixture into a pressure-sealable vessel for extended higher temperature treatment to effect the removal of secondary protecting groups on the synthetic oligonucleotide. This two step process reduces the quantity of support related contaminants in the final isolated product.

BRIEF SUMMARY OF THE INVENTION

The present invention is directed to an improved column for use in solid phase synthesis or purification. In a specific embodiment, the column is a disposable plastic column for use in solid phase synthesis or purification of complex chemicals, such as biomolecules and more specifically oligonucleotides.

In some embodiments, the column has a top orifice with a sufficient diameter so that a fluid line or a multiple fluid line bundle may dispense fluids into the column with great efficiency. The column has an upper cavity portion configured and sized to render it compatible with dispensing pippetors, so that it can be used as a pipette tip or a pipettor can be used to aspirate the column. The column has a lower cavity portion with a shoulder for ready placement of a lower frit to contain the solid support in a central cavity portion of the column which has a uniform cross-section. An upper frit can be conveniently placed in the uniform central cavity portion to seal the solid phase resin. The lower end tip of the column is configured as a luer-type fitting to provide a male luer connection. The upper cavity portion is configured to interface with the male luer of another column, so that two or more columns to be connected conveniently in series.

In accordance with an aspect of the present invention, a column for solid phase processing comprises a housing including a cavity extending from a top orifice at an upper end to a bottom orifice at a lower end which is smaller than the top orifice at the upper end. The cavity decreases in cross-sectional size from the top orifice at the upper end to the bottom orifice at the lower end. The lower end of the housing is configured as a male luer.

In some embodiments, the cavity of the housing includes an upper cavity portion adjacent the top orifice, a central cavity portion which is smaller in cross-section than the upper cavity portion, and a lower cavity portion which is smaller in cross-section than the central cavity portion and adjacent the bottom orifice. In specific embodiments, the top orifice is at least about 5 mm in diameter. The top orifice may be at most about 9 mm in diameter. The cavity is typically circular in cross-section.

In accordance with another aspect of the present invention, a column for solid phase processing comprises a housing including a cavity extending from a top orifice at an upper end to a bottom orifice at a lower end which is smaller than the top orifice at the upper end. The cavity decreases in cross-sectional size from the top orifice at the upper end to the bottom orifice at the lower end. The lower cavity portion includes a shoulder to support a lower frit for containing a solid support to occupy a portion of the central cavity portion. The central cavity portion has a uniform cross-section for receiving an upper frit to seal the solid support.

In accordance with another aspect of the invention, a column for solid phase processing comprises a housing including a cavity extending from a top orifice at an upper end to a bottom orifice at a lower end which is smaller than the top orifice at the upper end. The cavity includes an upper cavity portion adjacent the top orifice, a lower cavity portion adjacent the bottom orifice, and a central cavity portion between the upper cavity portion and the lower cavity portion. The lower end of the housing is configured as a male luer. The upper cavity portion is shaped to receive a male luer at a lower end of a housing of another column for connecting the columns in series.

In some embodiments, the upper cavity portion is tapered inward decreasing in cross-sectional size from the top orifice.

BRIEF DESCRIPTION OF THE DRAWINGS

FIG. 2 is a cross-sectional view of the column of FIG. 1 illustrating a solid support contained in the column;

FIG. 3 is a cross-sectional view illustrating the connection of a pair of columns in series;

DESCRIPTION OF THE SPECIFIC EMBODIMENTS

Figure 1:
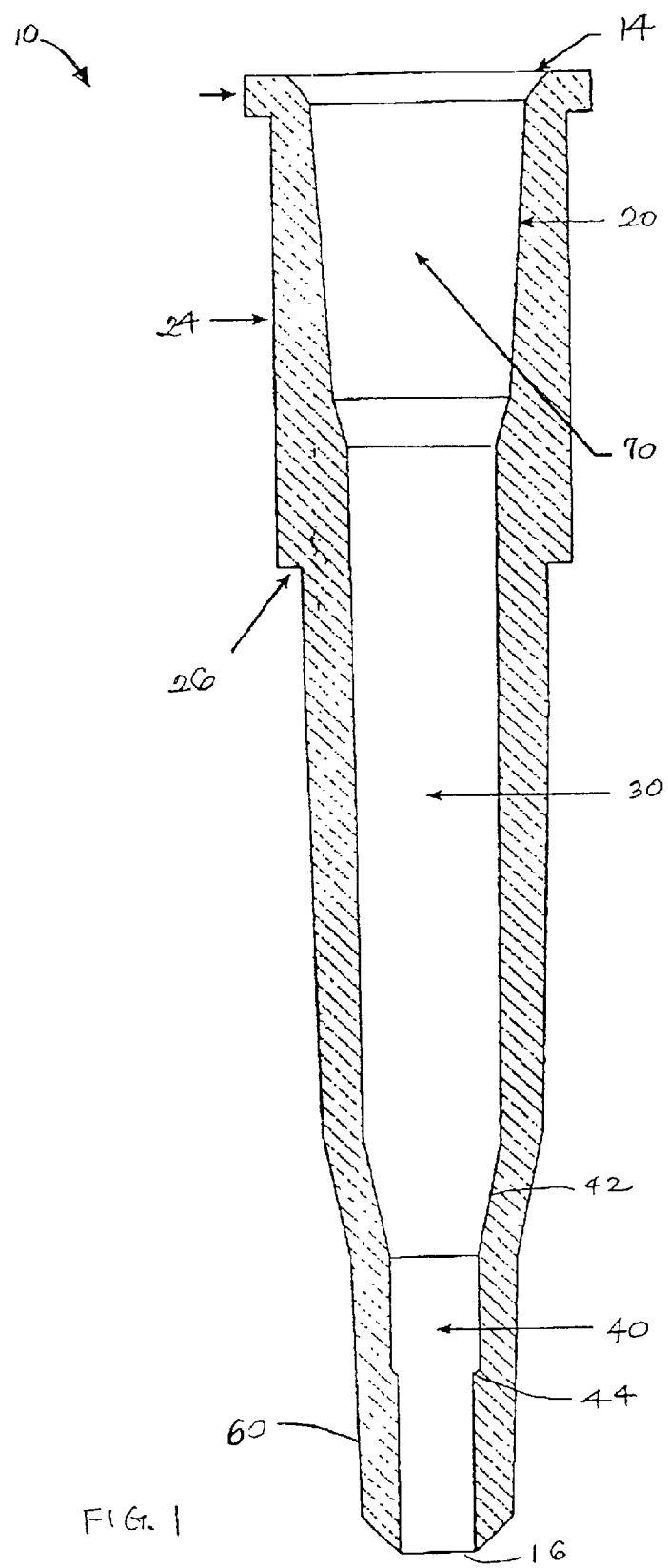
FIG. 1 is a cross-sectional view of a column in accordance with an embodiment of the present invention.

The present invention is directed to a column for solid phase processing. One embodiment of a column 10 is shown in FIG. 1. The column 10 includes a cavity extending from an upper end to a lower tip. The column 10 is circular in cross-section and the cross-section of the cavity decreases in size from the upper end to the lower tip. At the upper end, the column 10 desirably has a relatively large upper or top orifice 14 to provide a sufficient target such that a fluid line or a multiple fluid line bundle may dispense fluids into the column 10 with great efficiency. In one example, the upper orifice 14 is at least about 5 mm in diameter. In one preferred embodiment, the upper orifice 14 is sufficiently small to allow packing of standard 8×12 microtiter arrays. For example, the upper orifice 14 is no greater than about 9 mm in diameter. The bottom orifice 16 at the lower tip is smaller in size, typically substantially smaller in size, than the top orifice 14.

As shown in FIG. 1, the cavity includes an upper cavity portion 20 which desirably has internal dimensions rendering it compatible with dispensing pippetors, so that it can be used as a pipette tip or a pipettor can be used to aspirate the column 10. Moreover, such dimensions will allow for capping of the column 10 with available standard caps. In the embodiment shown, the upper cavity portion 20 is tapered with a decreasing diameter extending downward. The column 10 may include an untapered upper head 24 on which an identifying label or barcode can be applied manually or by an automatic device. A shoulder 26 may also be provided below the upper head 24 having a size (e.g., a diameter of about 0.25 inch) which facilitates use with compatible DNA synthesizers.

The central cavity portion 30 typically is smaller in diameter than the upper cavity portion 20. In the embodiment shown, the central cavity portion 30 has a uniform diameter. The central cavity portion 30 transitions to the lower cavity portion 40 with a decrease in diameter via a taper 42.

The lower cavity portion 40 desirably includes a shoulder 44 for ready placement of a lower frit 50 as shown in FIG. 2. The lower frit 50 is provided to contain the solid support 52 of the column 10, which fills a portion of the central cavity portion 30. An upper frit 54 is disposed in the central cavity portion 30 and placed on top of the solid support 52 to seal the solid phase resin while allowing fluid flow across the bed of resin. The uniform cross-section of the central cavity portion 30 conveniently allows the sealing of the solid support 52 by the upper frit 50 at varying levels as determined by the amount of solid phase resin.

As shown in FIGS. 1 and 2, the lower tip 60 of the column 10 desirably is configured as a luer-type fitting to provide a male luer connection. In a specific embodiment, the column 10 includes an interior throat 70 at the upper cavity portion 20 which is configured to interface with the male luer 60' of another column 10', as illustrated in FIG. 3. This allows two or more columns to be connected in series without the need for an adaptor or other third party connecting pieces. Different columns in the series may be used for different functions such as synthesis, purification, capture, and the like.

Figure 4:
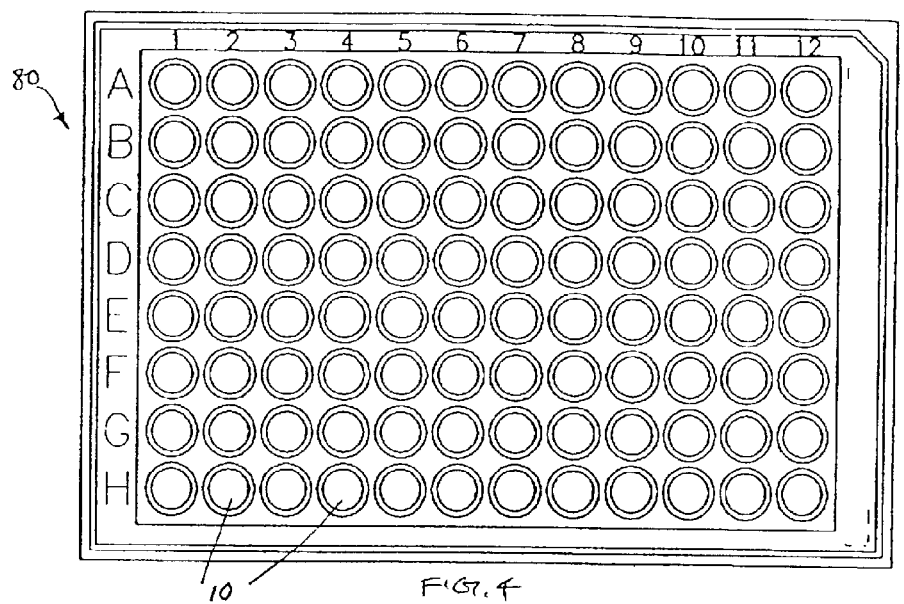
FIG. 4 is a top plan view of an array of columns.

The column 10 may be used individually, or a plurality of columns may be clustered in arrays which may be addressed by robotic fluid dispensers. FIG. 4 shows an example of an array 80 of columns 10.

Figure 5:
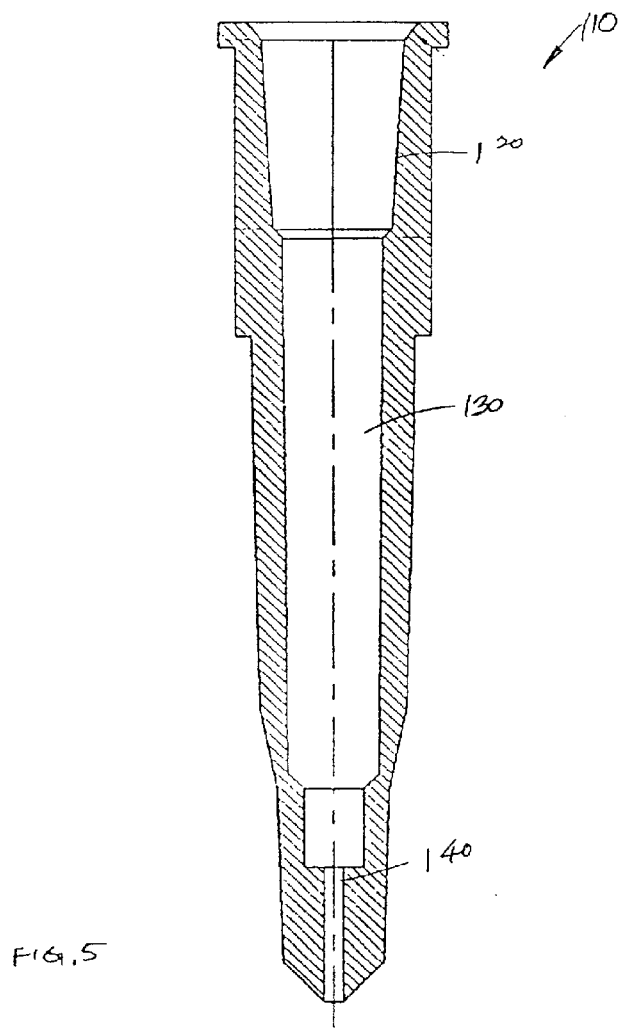
FIG. 5 is a cross-sectional view of a column in accordance with another embodiment of the present invention.

FIGS. 1–3 show one embodiment of the column 10. The dimensions and shapes of the column in other embodiments may vary. For instance, FIG. 5 shows another embodiment of the column 10 having an upper cavity portion 120, a central cavity portion 130, and a lower cavity portion 130. As compared to the column 10, the central cavity portion 130 is longer than the central cavity portion 30, and the lower cavity portion 140 is smaller in diameter than the lower cavity portion 40. In some embodiments, the columns may have a size that allows to be conveniently placed in standard Eppendorf centrifuge or the like for spinning down the content.

The above-described arrangements of apparatus and methods are merely illustrative of applications of the principles of this invention and many other embodiments and modifications may be made without departing from the spirit and scope of the invention as defined in the claims. The scope of the invention should, therefore, be determined not with reference to the above description, but instead should be determined with reference to the appended claims along with their full scope of equivalents.

What is claimed is:

1. A column for solid phase processing, the column comprising a housing including a cavity extending from a top orifice at an upper end to a bottom orifice at a lower end which is smaller than the top orifice at the upper end, the cavity decreasing in cross-sectional size from the top orifice at the upper end to the bottom orifice at the lower end, the lower end of the housing being configured as a male luer;

wherein the cavity of the housing includes an upper cavity portion adjacent the top orifice, a central cavity portion smaller in cross-section than the upper cavity portion, and a lower cavity portion smaller in cross-section than the central cavity portion and adjacent the bottom orifice; and wherein the upper cavity portion is tapered inward decreasing in cross-sectional size from the top orifice, and wherein a female luer taper is spaced from the top orifice and is disposed in the upper cavity portion near the central cavity portion.

2. The column of claim 1 wherein the lower cavity portion includes a shoulder for supporting a lower frit.

3. The column of claim 1 wherein the central cavity portion has a uniform cross-section.

4. The column of claim 1 wherein the upper cavity portion is shaped to receive a male luer at a lower end of a housing of another column for connecting the columns in series.

5. The column of claim 1 wherein the top orifice is at least about 5 mm in diameter.

6. The column of claim 1 wherein the top orifice is at most about 9 mm in diameter.

7. The column of claim 1 wherein the cavity is circular in cross-section.

8. A column for solid phase processing, the column comprising a housing including a cavity extending from a top orifice at an upper end to a bottom orifice at a lower end which is smaller than the top orifice at the upper end, the cavity decreasing in cross-sectional size from the top orifice at the upper end to the bottom orifice at the lower end, the lower cavity portion including a shoulder to support a lower frit for containing a solid support to occupy a portion of the central cavity portion, the central cavity portion having a uniform cross-section for receiving an upper frit to seal the solid support;

wherein the upper cavity portion is tapered inward decreasing in cross-sectional size from the top orifice to form an interior throat which is sufficiently long to interface with a male luer of another column inserted into the upper cavity portion and which is tapered and spaced from the top orifice.

9. The column of claim 8 wherein the top orifice is between about 5 mm and 9 mm in diameter.

10. The column of claim 8 wherein the lower end of the housing is configured as a male luer.

11. The column of claim 10 wherein the upper cavity portion is shaped to receive a male luer at a lower end of a housing of another column for connecting the columns in series.

12. The column of claim 8 wherein the top orifice has a diameter of at least about 5 mm and at most about 9 mm.

13. A column for solid phase processing, the column comprising a housing including a cavity extending from a top orifice at an upper end to a bottom orifice at a lower end which is smaller than the top orifice at the upper end; the cavity including an upper cavity portion adjacent the top orifice, a lower cavity portion adjacent the bottom orifice, and a central cavity portion between the upper cavity portion and the lower cavity portion; the lower end of the housing being configured as a male luer, the upper cavity portion being shaped to receive a male luer at a lower end of a housing of another column for connecting the columns in series;

wherein the upper cavity portion is tapered inward decreasing in cross-sectional size from the top orifice, and wherein a female luer taper is spaced from the top orifice and is disposed in the upper cavity portion near the central cavity portion to mate with a male luer of another column.

14. The column of claim 13 wherein the top orifice is at least about 5 mm in diameter.

15. The column of claim 13 wherein the cavity decreases in cross-sectional size from the top orifice at the upper end to the bottom orifice at the lower end.

16. The column of claim 15 wherein the central cavity portion is smaller in cross-section than the upper cavity portion, and the lower cavity portion is smaller in cross-section than the central cavity portion.

17. The column of claim 13 wherein the central cavity portion has a uniform cross-section.

18. The column of claim 13 wherein the lower cavity portion includes a shoulder for supporting a lower frit.

19. The column of claim 13 wherein the top orifice is at most about 9 mm in diameter.

* * * * *